(12) United States Patent
Markussen

(10) Patent No.: US 6,602,843 B2
(45) Date of Patent: Aug. 5, 2003

(54) ENZYME CONTAINING GRANULE

(75) Inventor: Erik Kjær Markussen, Væløse (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/035,884

(22) Filed: Nov. 9, 2001

(65) Prior Publication Data

US 2002/0160927 A1 Oct. 31, 2002

Related U.S. Application Data

(63) Continuation of application No. 09/872,922, filed on Jun. 1, 2001, now Pat. No. 6,348,442, which is a continuation of application No. 09/344,877, filed on Jun. 25, 1999, now Pat. No. 6,268,329.

(60) Provisional application No. 60/092,003, filed on Jul. 8, 1998.

(30) Foreign Application Priority Data

Jun. 30, 1999  (DK) .......................... 1998 00876

(51) Int. Cl.$^7$ ............................ C11D 7/08; C11D 7/16; C11D 7/40; C11D 17/00
(52) U.S. Cl. ................... 510/392; 510/320; 510/321; 510/441; 510/443; 510/446; 510/530
(58) Field of Search ..................... 510/320, 321, 510/392, 441, 443, 446, 530; 134/42

(56) References Cited

U.S. PATENT DOCUMENTS 6,268,329 B1 * 7/2001 Markussen .................. 510/392
6,348,442 B2 * 2/2002 Markussen .................. 510/392

FOREIGN PATENT DOCUMENTS

EP          206417      * 12/1986

* cited by examiner

*Primary Examiner*—Gregory Delcotto
(74) *Attorney, Agent, or Firm*—Elias J. Lambiris; Jason I. Garbell

(57) ABSTRACT

This invention relates to an enzyme containing granular composition comprising:
  a) an enzyme containing core and
  b) a protective substantially continuous layer or coating encapsulating the core comprising at least 60% of a water soluble compound, having a molecular weight below 500 grams per mole, a pH below 11 and a constant humidity at 20° C. of more than 81%.

The invention provides an improved stability of enzymes upon storage.

22 Claims, 1 Drawing Sheet

ENZYME CONTAINING GRANULE

CROSS-REFERENCE TO RELATED APPLICATIONS

This application is a continuation application of U.S. application Ser. No. 09/872,922 filed on Jun. 1, 2001, now U.S. Pat. No. 6,348,442, which is a continuation of U.S. application Ser. No. 09/344,877, filed Jun. 25, 1999, now U.S. Pat. No. 6,268,329, and claims, under 35 U.S.C. 119, priority of Danish application no. PA 1998 00876, filed Jun. 30, 1999, and benefit of U.S. provisional application No. 60/092,003, filed Jul. 8, 1998. Priority from U.S. application Ser. No. 09/344,877, filed on Jun. 25, 1999, is claimed under 35 U.S.C. 120, the contents of which are fully incorporated herein by reference

FIELD OF THE INVENTION

The present invention relates to an enzyme containing granule protecting the enzyme from inactivation when the granules are stored, i.e. improving the storage stability of the enzyme. The invention further relates to a process for producing such a granule and to the use of the granule in a number of industrial applications such as incorporation of the granule in a detergent composition.

BACKGROUND OF THE INVENTION

The industrial use of enzymes, notably enzymes of microbial origin, has become increasingly common. Enzymes are used in numerous industries, including, for example, the starch-processing industry and the detergent industry.

It is well known that enzymes upon storage is liable to be degraded or inactivated by components (such as oxygen or bleach components) from the surrounding matrix (such as a detergent), which are capable of oxidizing or otherwise inactivating the enzyme. Further it is well known that a low formation of enzyme-containing dust of granules is desired.

Since the introduction of enzymes into the detergent industry, a lot of effort has been devoted to improving the formulation of enzyme products by applying granulation and coating of the enzyme so as to both protect the enzyme from degradation as well as control enzyme dust formation.

Many granulates are composed of a core particle upon which an enzyme containing layer is added. The core may also in itself contain enzyme. To apply the desired properties of this construction, e.g. color, dust formation, solubility rate, size, enzyme stability, physical strength etc. the core-enzyme construction is usually added additional layers of coatings providing such properties.

Some coating layers described in the art are complex multi-component compositions such as in:

WO 90/09440 which discloses an enzyme containing granulate 1) one coating (or shell) comprising a binder (e.g. kaolin), a filler (e.g. inorganic salts), granulating agents (e.g. cellulose fibers providing physical strength), and an enzyme and 2) a second dust suppressing coating (mono-, di- or triglyceride).

DE 4322229 which discloses an enzyme containing granule with a coating comprising an inorganic pigment, an alcohol, an emulsifier, a pigment dispersant and water.

JP 61162185 which discloses a process for production of an enzyme containing granule comprising coating a core with a solution containing enzyme(s), sodium sulfate and optionally binders and coating agents.

Other coating layers apply polymers or even macroscopic particles to gain improved properties of the granulate such as:

WO 97/23606 which discloses an enzyme containing granule comprising an outer coating of polyvinyl pyrrolidone, PVA or PEG.

WO 96/38527 which discloses an enzyme containing granulated substance with a coating comprising water insoluble particles and a binder.

U.S. Pat. No. 5,324,649 which discloses an enzyme containing granule comprising an outer coating of polyvinyl alcohol or a copolymer.

WO 93/07263 which discloses an enzyme containing granule comprising an outer coating of vinyl (co)polymer.

WO 92/12645 which discloses an enzyme containing T-granulate coated with high melting fat or wax.

WO 89/08694 which discloses an enzyme containing granulate with a coating comprising a mono- or diglyceride of a fatty acid.

DD 263790 which discloses a protease containing granule with a coating of skim milk and/or maltodextrin.

WO 87/07292 which discloses an enzyme containing granulate with a coating containing a copolymers of acrylic acid, and/or an filler and/or a plasticiser.

EP 193829 and U.S. Pat. No. 4,689,297 which discloses a process for production of an enzyme containing particle comprising coating the particle with a macromolecular, film forming water soluble or water dispersible coating agent.

JP 58179492 which discloses an enzyme supporting particle with a coating of modified cellulose.

WO 89/08695 which discloses an enzyme containing particles with a coating containing clay.

Still other prior art disclosures apply non aqueous liquids as coatings to gain improved properties of the granulate such as:

WO 96/16151 which discloses a enzyme containing granule with a coating of a non-aqueous liquid.

Some prior art disclosures mention use of agents in a coating layers providing a special functions upon dissolution of the granulates such as:

DE 4344215 which discloses an enzyme containing granule with a coating containing an inorganic Ag-corrosion inhibitor.

EP 206417 which discloses an enzyme containing granule with a coating containing an alkaline buffer salt having a pH of 7–11. The buffer salt may constitute 50–100% of the coating.

WO 93/07263 discloses an enzyme containing granule which contains a scavenger layer, preferably ammonium sulfate.

EP-415652-A2 as well as U.S. Pat. No. 5,093,021 describes enzyme granules coated with unsoluble and highly alkaline alkali metal silicates optionally in combination with alkali metal carbonates.

Use of low molecular water soluble compounds in coatings in moderate amounts have been disclosed within the art of formulating stabile enzyme compositions usually as filler material. However, it has not been acknowledged that the amount and hygroscopicity of such compounds has essential impact on the stability of an enzyme in an enzyme granule coated with such compounds.

SUMMARY OF THE INVENTION

We have in our search for enzyme formulation with improved enzyme stability surprisingly found, that an enzyme containing granule coated or encapsulated by a continuous layer of a simple, predominantly water soluble and low cost material with a high constant humidity significantly increases the storage stability of the enzyme, especially at high humidity conditions.

The present invention provides thus in a first aspect an enzyme containing granule comprising:

a) an enzyme containing core and
b) a protective substantially continuous layer or coating encapsulating the core comprising at least 60% of a water soluble compound, having a molecular weight below 500 grams per mole, a pH below 11 and a constant humidity at 20° C. of more than 81%.

In accordance with the first aspect a second aspect of the invention is a method for producing said enzyme containing granule comprising coating said enzyme containing core with said coating material.

In accordance with the previous aspects further aspects of the invention relates to applications of the enzyme containing granules, e.g. incorporation of the granule in a detergent or an animal feed composition or a baking composition and a cleaning method comprising contacting an object with an aqueous solution of the enzyme containing granule.

DETAILED DESCRIPTION OF THE INVENTION

Definitions

Figure 1:
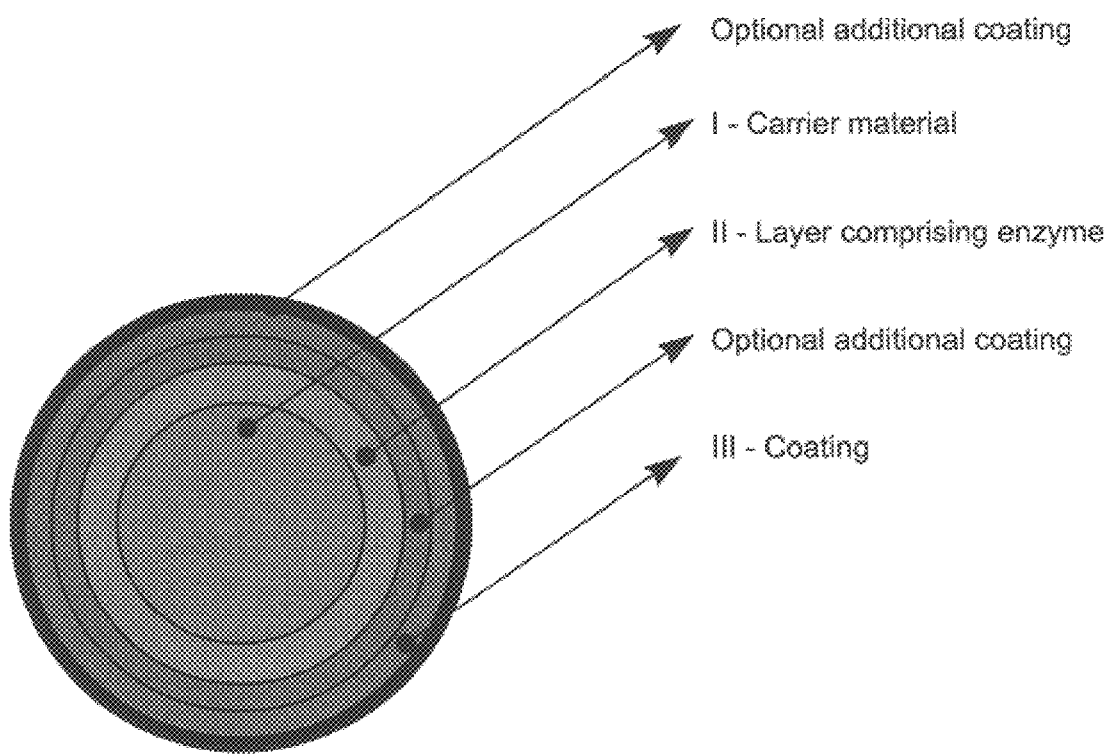
FIG.1 shows a cross section of an example of a granule according to the invention depicting different granule layers.

The term "% RH" is used throughout the text, and in the context of the invention the term is to be understood as the relative humidity of air. 100% RH is air saturated with water moisture at a fixed temperature and % RH thus reflects the percent moisture saturation of the air.

The term "constant humidity" (in the context of the invention sometimes abbreviated as CH) of a compound or substance is to be understood as the % RH of atmospheric air in equilibrium with a saturated aqueous solution of said compound in contact with the solid phase of said compound, all confined within a closed space at a given temperature. This definition is in accordance with "Handbook of chemistry and physics" CRC Press, Inc., Cleveland, USA, 58th edition, p E46, 1977–1978. Accordingly $CH_{20° C.}$=50% for a compound means that air with a 50% humidity will be in equilibrium with a saturated aqueous solution of the compound at 20° C. Accordingly the term constant humidity is a measure of the hygroscopic properties of a compound.

The term "pH" of a compound in the context of the invention is to be understood as the pH of a 10% w/w aqueous solution of the said compound.

The term "water soluble compound" in the context of the invention is to be understood as a compound for which at least 0.1 grams of the compound may dissolved in 100 g of water at 20° C., preferably at least 0.5 g per 100 g water, e.g. at least 1 g per 100 g water.

The Protective Coating

Without being bound to this theory we believe that a coating with a high constant humidity value has at least one important functional property: The coating inhibits moisture from entering the enzyme containing core material. The coating is thus a barrier between the potentially harmful matrix which surrounds the enzyme containing granules (e.g. a detergent and/or air). For moisture and/or harmful components carried by the moisture to reach the enzyme within a granule, the moisture must pass through the coating (i.e. the moisture must be absorbed on the outside and liberated on the inside surface of the coating) before coming in contact with and inactivating the enzyme. Coatings with a high constant humidity (CH) thus provides a better protection of the enzyme than coatings with a lower constant humidity, i.e. the high humidity constant coating will inhibit moisture from entering the granule at a broader ranger of humidity conditions (% RH) of the surrounding matrix. We believe that if as an example the % RH is higher than the CH of the coating material the coating will absorb moisture from the surrounding matrix and allow the moisture to be transported inside the granule.

For coatings allowing absorption of moisture from the surrounding matrix, the rate of moisture absorption, and thus the damaging affects on the enzyme is believed to be further increased if the core material also readily absorbs the incoming moisture, which is the case for many known core materials. The moisture absorption process may thus be accelerated by swelling or expansion of the core materials forming cracks, holes or disruptions in the coating, thus making moisture access to the enzyme in the core even easier. Choosing a coating with a constant humidity value higher than the expected % RH of the surrounding air thus effectively reduces this process.

Further a coating with a high constant humidity value is believed to inhibit entry of microorganisms thus reducing the possibility of microbial growth within the granule.

As mentioned vide supra a suitable coating according to the invention comprises at least 60% w/w of a water soluble compound, having a molecular weight below 500 grams per mole, a pH below 11 and a constant humidity of more than 81% w/w. Water soluble compounds having a molecular weight below 500 g/mole are usually much cheaper and easier to handle with respect to coating processes than high molecular substances such as polymers. Preferred water soluble compounds should have a molar weight in the range of 30–500 g/mole preferably 75–400, e.g. 100–300 g/mole.

Further a water soluble compound benefits release and/or dissolution of the enzyme upon introduction of the granule in an aqueous medium (e.g. a cleaning or washing liquor) much more than insoluble salts such as calcium carbonate and minerals or inorganic compounds such as kaolin and/or titandioxide. Accordingly a preferred water soluble compound is an inorganic salt, e.g. salts of sulfate, sulfite, phosphate, phosphonate, nitrate, chloride or carbonate or salts of simple organic acids (less than 10 carbon atoms e.g. 6 or less carbon atoms) such as citrate, malonate or acetate. Preferred cations in these salt are alkali or earth alkali metal ions, although the ammonium ion or metal ions of the first transition series, e.g. Zinc may also be used. Especially alkali- or earth alkali metal salts of sulfate, sulfite, phosphate, phosphonate, nitrate, chloride or carbonate or salts of simple organic acids such as citrate, malonate or acetate are preferred.

A suitable solubility should be that at least 0.1 grams of the salt in 100 g of water at 20° C., preferably at least 0.5 g per 100 g water, e.g. at least 1 g per 100 g water. In a most preferred embodiment of the invention the solubility of the water soluble compound is at least 10 grams or at least 20 grams of compound per 100 gram water at 20° C. A high solubility is very advantageous as it benefits the coating process as it lowers the amount of water needed to be evaporated after delivering the coating on the core. Further it is important that the compound is dissolved in an aqueous phase before coating, because if a core is coated by applying the water soluble compound in dry form as a particulate powder or as a slurry on the core, these particles will form channels or openings in the coating allowing access of moisture to the core.

The water soluble compound should also have a moderate pH in aqueous solution as extreme pH values of coating solution may corrode equipment as well as being potentially dangerous to work with. Thus the water soluble compound may be a slightly alkaline or slightly acidic compound. Accordingly the pH of the water soluble compound should be below 11, preferably below 10, e.g. below 9, below 8 or even below 7, when measured as a 10% w/w aqueous solution of the water soluble compound. Some soluble salts like sodium carbonate has a very high pH (above 11) and may not be suitable as a coating material in the context of this invention. Also bicarbonate salts may be unsuitable as they although they have a lower pH tend to form carbon dioxide gas in solution which may interfere with the coating process.

Specific examples of suitable water soluble compounds of the invention are $Na_2HPO_4$ ($CH_{20°\ C.}$=95%), $Na_3PO_4$ ($CH_{25°\ C.}$=92%), ($NH_4$) $H_2PO_4$ $CH_{20°\ C.}$=93.1%), $KH_2PO_4$ ($CH_{20°\ C.}$=92%), $Na_2SO_4$($CH_{20°\ C.}$=93%), $K_2SO_4$($CH_{25°\ C.}$=99%), $KHSO_4$ ($CH_{20°\ C.}$=86%), $ZnSO_4$ ($CH_{20°\ C.}$=90%) and sodium citrate ($CH_{25°\ C.}$=86%). Sodium sulfate and sodium citrate are the most preferred water soluble compounds as they are cheap chemicals.

The coating comprises as said at least 60% w/w, e.g. 65% w/w or 70% w/w of the water soluble compound, which preferably may be at least 75% w/w, e.g. at least 80% w/w, at least 85% w/w, e.g. at least 90% w/w or at least 95% w/w. The coating may even essentially consist of the water soluble compound. With due respect for maintaining a desired suitable constant humidity value for the total coating material minor amounts of other feasible compounds may be present in the coating such as conventional coating materials. Examples of are, inter alia, described in the paragraph "additional coatings" given below. Other examples of conventional coating materials may be found in references such as U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A and/or JP 58179492

In a particular embodiment the coating may comprise minor amounts of a protective agent capable of reacting with a component capable of inactivating (being hostile to) the enzyme entering the granule from the surrounding matrix, i.e. before the component come into contact and inactivate the enzyme. The protective agent may thus e.g. be capable of neutralizing, reducing or otherwise reacting with the hostile component rendering it harmless to the enzyme. Typical components capable of inactivating the enzyme are oxidants such as perborates, percarbonates, organic peracids and the like.

Protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, -carbonates or bicarbonates which provide a chemical scavenging effect by actively neutralizing e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). Most preferred agents are salts of thiosulfates, e.g. sodium thiosulfate. The amounts of protective agent in the coating may be 1–40% w/w of the coating, preferably 5–30%, e.g. 10–20%.

In accordance with the concept of the invention the coating does not contain any enzyme, as the purpose of the coating is to protect enzymes encapsulated by the coating.

The protective effect of the coating depends on the thickness of the coating and the amount of coating relative to the rest of the enzyme containing granule. An increased coating thickness provides a better protection of the enzyme, but at the same time result in increased manufacturing costs as well as a risk of poorer granule properties with respect to enzyme solubility rate upon introduction of the enzyme containing granule in an aqueous medium. For effective protection the coating thickness also must be adjusted to the size of the core, e.g. to obtain a desired size of the finishes granule. Depending on the size of the core material the coating may be applied in 1–75% w/w of the weight of the coated granule to obtain a desired size of the coated granule. For small sizes of core material the coating may be applied in 50–75% w/w or 15–50% of the coated granule. Usually coatings constituting 2–20% w/w, preferably 3–10% w/w, e.g. 6% of the coated granule is however preferred.

The coating should encapsulate the enzyme containing core by forming a substantially continuous layer. The layer or coating is preferably homogenous in thickness and by substantially continuous is meant that the core surface should have few or none uncoated areas.

The Core

The core contains the enzyme(s). Besides of the enzyme (s) the core may be constructed in any way or of any material which provides the desired functional properties of the core material, e.g. the core may consist of materials which allows readily release of the enzyme(s) upon introduction to an aqueous medium. In one preferred embodiment the core is constructed of a particulate carrier (I) with the enzyme absorbed and/or an enzyme containing layer (II) applied on the carrier surface, optionally comprising an enzyme protecting reducing agent. There may even be additional coating within the core material providing desired functional properties of the core material. Another preferred core is the so called T-granulate wherein enzyme and granulation material is mixed to form granules incorporating the enzyme distributed throughout the core such as described in U.S. Pat. No. 4,106,991 e.g. Example 1. Any conventional methods and non-enzyme materials may be used to prepare the core. Examples of known conventional cores and materials is, inter alia, described in, U.S. Pat. No. 4,106,991 (in particular), EP 170360, EP 304332, EP 304331, EP 458849, EP 458845, WO 97/39116, WO 92/12645, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A, JP 58179492.

As a particularly preferred embodiment of the invention the core may be prepared by applying an enzyme layer onto a "placebo" carrier (enzyme-free carrier) according to the methodology described in U.S. Pat. No. 4,106,991. Optionally additional enzyme may be absorbed into the surface of the carrier.

In a particular embodiment of the invention the enzyme containing core may also comprise a protective agent as described for the coating, vide supra, preferably mixed with the enzyme in suitable amounts such as 0.1–1% w/w of the coated granule, preferably 0.1–0.5% w/w, e.g. 0.33% w/w.

As described, supra, the core may through the coating absorb moisture from the surrounding environment, a process which may cause the core to swell resulting in crack formation in the coating and further moisture absorbance. The core may even in at high relative humidity dissolve and become fluid. Accordingly in order to provide further stabilization of the enzyme the core should preferably be a non absorbing core, i.e. the should only be able of absorbing less moisture than 20% w/w of it own dry weight, preferably less than 10% w/w, e.g. less than 8% w/w or less than 5% w/w, measured at 75% RH at 20° C.

Enzymes

The enzyme in the context of the present invention may be any enzyme or combination of different enzymes, which benefits from being granulated and thus be protected against a hostile environment in order to be applicable for a specific use. Accordingly, when reference is made to "an enzyme" this will in general be understood include combinations of one or more enzymes.

It is to be understood that enzyme variants (produced, for example, by recombinant techniques) are included within the meaning of the term "enzyme". Examples of such enzyme variants are disclosed, e.g., in EP 251,446 (Genencor), WO 91/00345 (Novo Nordisk A/S), EP 525,610 (Solvay) and WO 94/02618 (Gist-Brocades NV).

The enzyme classification employed in the present specification with claims is in accordance with *Recommendations (1992) of the Nomenclature Committee of the International Union of Biochemistry and Molecular Biology*, Academic Press, Inc., 1992.

Accordingly the types of enzymes which may appropriately be incorporated in granules of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-)

Preferred oxidoreductases in the context of the invention are peroxidases (EC 1.11.1), laccases (EC 1.10.3.2) and glucose oxidases (EC 1.1.3.4)], while preferred transferases are transferases in any of the following sub-classes:

a) Transferases transferring one-carbon groups (EC 2.1);
b) transferases transferring aldehyde or ketone residues (EC 2.2); acyltransferases (EC 2.3);
c) glycosyltransferases (EC 2.4);
d) transferases transferring alkyl or aryl groups, other that methyl groups (EC 2.5); and
e) transferases transferring nitrogenous groups (EC 2.6).

A most preferred type of transferase in the context of the invention is a transglutaminase (protein-glutamine glutamyltransferase; EC 2.3.2.13).

Further examples of suitable transglutaminases are described in WO 96/06931 (Novo Nordisk A/S).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as Δ-amylases (EC 3.2.1.1); peptidases (EC 3.4, also known as proteases); and other carbonyl hydrolases].

In the present context, the term "carbohydrase" is used to denote not only enzymes capable of breaking down carbohydrate chains (e.g. starches) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): Δ-amylases (3.2.1.1), E-amylases (3.2.1.2), glucan 1,4-Δ-glucosidases (3.2.1.3), cellulases (3.2.1.4), endo-1,3(4)-E-glucanases (3.2.1.6), endo-1,4-E-xylanases (3.2.1.8), dextranases (3.2.1.11), chitinases (3.2.1.14), polygalacturonases (3.2.1.15), lysozymes (3.2.1.17), E-glucosidases (3.2.1.21), Δ-galactosidases (3.2.1.22), E-galactosidases (3.2.1.23), amylo-1,6-glucosidases (3.2.1.33), xylan 1,4-E-xylosidases (3.2.1.37), glucan endo-1,3-E-D-glucosidases (3.2.1.39), Δ-dextrin endo-1,6-Δ-glucosidases (3.2.1.41), sucrose Δ-glucosidases (3.2.1.48), glucan endo-1,3-Δ-glucosidases (3.2.1.59), glucan 1,4-E-glucosidases (3.2.1.74), glucan endo-1,6-E-glucosidases (3.2.1.75), arabinan endo-1,5-Δ-L-arabinosidases (3.2.1.99), lactases (3.2.1.108), chitosanases 3.2.1.132) and xylose isomerases (5.3.1.5).

Examples of commercially available oxidoreductases (EC 1.-.-.-) include Gluzyme□ (enzyme available from Novo Nordisk A/S). Further oxidoreductases are available from other suppliers.

Examples of commercially available proteases (peptidases) include Esperase□, Alcalase□, Neutrase□, Durazym□, Savinase□, Kannase, Pyrase□, Pancreatic Trypsin NOVO (PTN), Bio-Feed□ Pro and Clear-Lens□ Pro (all available from Novo Nordisk A/S, Bagsvaerd, Denmark).

Other commercially available proteases include Maxatase□, Maxacal□, Maxapem□, Opticlean□ and Purafect□ (available from Genencor International Inc. or Gist-Brocades).

Examples of commercially available lipases include Lipolase□, Lipolase□ Ultra, LipoPrime, Lipozyme□, Palatase□, Novozym□ 435 and Lecitase□ (all available from Novo Nordisk A/S).

Other commercially available lipases include Lumafast□ (*Pseudomonas mendocina* lipase from Genencor International Inc.); Lipomax□ (Ps. pseudoalcaligenes lipase from Gist-brocades/Genencor Int. Inc.; and Bacillus sp. lipase from Solvay enzymes. Further lipases are available from other suppliers.

Examples of commercially available carbohydrases include Alpha-Gal□, Bio-Feed□ Alpha, Bio-Feed□ Beta, Bio-Feed□ Plus, Bio-Feed□ Plus, Novozyme□ 188, Celluclast□, Cellusoft□, Ceremyl□, Citrozym□, Denimax□, Dezyme□, Dextrozyme□, Finizym□, Fungamyl□, Gamanase□, Glucanex□, Lactozym□, Maltogenase□, Pentopan□, Pectinex□, Promozyme□, Pulpzyme□, Novamyl□, Termamyl□, AMG□ (Amyloglucosidase Novo), Maltogenase□, Sweetzyme□ and Aquazym□ (all available from Novo Nordisk A/S). Further carbohydrases are available from other suppliers.

The amount of enzyme to be incorporated in a granule of the invention will depend on the intended use of the granulate. For many applications, the enzyme content will be as high as possible or practicable.

The content of enzyme (calculated as pure enzyme protein) in a granule of the invention will typically be in the range of from about 0.5% to 20% by weight of the core.

When, for example, a protease (or peptidase) is incorporated in granules according to the invention, the enzyme activity (proteolytic activity) of the finished granules will typically be in the range of 1–50 KiloNovoProteaseUnits per gram. Likewise, in the case of, for example, Δ-amylases, an activity of 10–500 KiloNovoUnits per gram will be typical, whilst for lipases, an activity in the range of 50–400 KiloLipolaseUnits per gram will normally be suitable. All units are known to the art.

Additional Coatings

The granules of the present invention may comprise one, two or more additional coating layers on the inside or outside surface of the protective coating according to the invention.

The additional coating layers may perform any of a number of functions in the granule, depending on the intended use of the granule. Thus, for example, an additional coating may achieve one or more of the following effects:
(i) further reduction of the dust-formation tendency of a granule without the additional coating according to the invention;
(ii) further protection of enzyme(s) in the granule against oxidation by bleaching substances/systems (e.g. perborates, percarbonates, organic peracids and the like);
(iii) dissolution at a desired rate upon introduction of the granule into a liquid medium (such as an aqueous medium);
(iv) provide a better physical strength of the granule.

Any additional conventional coating(s) of desired properties may be applied and examples of conventional coating materials and coating methods is, inter alia, described in U.S. Pat. No. 4,106,991, EP 170360, EP 304332, EP 304331, EP 458849, EP 458845, WO 97/39116, WO 92/12645, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A, JP 58179492

In appropriate embodiments of granules according to the present invention, the additional coating layer may be composed as described in U.S. Pat. No. 4,106,991 [e.g. with a waxy material such as polyethylene glycol (PEG), optionally followed by powdering with a whitener such as titanium dioxide].

Additional coating layers may further comprise one or more of the following: anti-oxidants, chlorine scavengers, plasticizers, pigments, lubricants (such as surfactants or antistatic agents) additional enzymes and fragrances.

Plasticizers useful in coating layers in the context of the present invention include, for example: polyols such as sugars, sugar alcohols, or polyethylene glycols (PEGs) having a molecular weight less than 1000; urea, phthalate esters such as dibutyl or dimethyl phthalate; and water.

Suitable pigments include, but are not limited to, finely divided whiteners, such as titanium dioxide or kaolin, coloured pigments, water soluble colorants, as well as combinations of one or more pigments and water soluble colorants.

As used in the present context, the term "lubricant" refers to any agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents.

Examples of suitable lubricants are polyethylene glycols (PEGs) and ethoxylated fatty alcohols.

In an especially preferred embodiment of the invention, only a lubricant is applied as additional coating. The composition of 1) an enzyme containing core, 2) a coating and 3) and an additional lubricant coating has shown particularly good properties with respect to enzyme stability.

Coating Methods

The invention also relates to a method for manufacture/production of the enzyme containing granule described herein. Conventional coating methods may be used to apply the coating according to the invention as described by the references stated in the previous section (above).

A method for production of the enzyme containing granule may comprise the following steps:
a) mixing an enzyme containing core material with a liquid medium comprising the water soluble compound of the invention and,
b) removing volatile components of the liquid medium from the mixture, so as to deposit the nonvolatile components of the liquid medium as solid coating layer on the core material.

In a preferred embodiment of the invention the enzyme containing granule is produced by a fluid bed process comprising:
a) fluidising an enzyme containing core material in a fluid bed apparatus,
b) introducing a liquid medium comprising the water soluble compound of the invention by atomization of the liquid medium into the fluid bed, so as to deposit nonvolatile components of the liquid medium as a solid coating layer on the core material and,
c) removing volatile components of the liquid medium from the coated core material.

In a further preferred embodiment of the invention the core material is prepared by a method comprising:
a) Preparing a particulate carrier material,
b) introducing a liquid medium comprising an enzyme by atomization of the liquid medium into the fluid bed, so as to deposit nonvolatile components including the enzyme of the liquid medium as an enzyme containing layer on the carrier, and
c) removing volatile components of the liquid medium from the core material.

The particulate carrier material may in a preferred embodiment comprise a binder (such as Glucidex☐ 21D, from Roquette Freres), a fibre material (such as cellulose fibres) and a filler (such as finely ground sodium sulfate and/or kaolin). The particulate carrier may as well be prepared/granulated and dried as described in Example 1 in U.S. Pat. No. 4,106,991. Following granulation the dry particulate carrier may suitably be sieved, and fractionated after size to obtain a uniform carrier size. Preferred carrier sizes measured as the diameter of the carrier are between 0.1–2 mm, e.g. 0.3–1.0 mm.

As a further preferred embodiment additional enzyme may be absorbed on the particulate carrier prior to applying the enzyme layer (II) This absorption may be achieved by:
a) absorbing the enzyme(s) into the surface of the carrier by contacting the particulate carrier with a liquid comprising the enzyme in a mixer,
b) mixing the composition by means of mixing blades, and
c) drying the enzyme loaded carrier by fluidising it in a fluid bed apparatus, Conventional mixing equipment can satisfactorily be used to mix the particulate carrier with the enzyme-containing liquid medium. The mixing equipment can be a batch mixer or a continuous mixer, such as a convective mixer [see, e.g., Harnby et al., *Mixing in the Process Industries*, pp. 39–53 (ISBN 0-408-11574-2)]. Non-convective mixing equipment, e.g. rotating drum mixers or so-called pan-granulators, may also be employed.

Drying of enzyme-loaded particulate carrier, application of the enzyme containing layer (II) the coating (III) and any additional coatings may be performed in any type of fluidising equipment (such as in a fluid-bed apparatus or other form of fluidizing equipment, such as a Huttlin-type fluidizer). For a description of suitable fluid-bed equipment, see, e.g., Harnby et al., *Mixing in the Process Industries*, pp. 54–77 (ISBN 0-408-11574-2).

Applications of the Enzyme Containing Granule

The enzyme containing granule according to the invention is useful where ever enzymes are to be stored alone or to be incorporated in another dry product, and an improved enzyme stability is needed to enable good storage properties (improved shelf life) of the granule. Especially at relatively humid conditions, i.e. under an atmosphere with a % RH of more than 55% RH, preferably more than 60% RH, e.g. more than 70% RH. Especially at conditions with more than 75% RH, more than 85% RH or more than 95% RH the invention is useful. The granule is also particularly useful in dry products comprising oxidative compounds such as peroxides or superoxides, e.g. bleach (e.g. perborates or percarbonates) or other reactive components, which in case of contact with the enzyme is able of inactivating the enzyme. Thus the invention provides a detergent composition comprising the granule of the invention. The enzyme containing granule is further useful for cleaning an object (e.g. textile of cotton or other natural or synthetic fabrics) by contacting the object with an aqueous solution of the enzyme containing granule. Finally the enzyme containing granule is useful in products such as animal feed/fodder or bakers flour.

Detergent Disclosure

A detergent composition of the invention comprises the enzyme containing granule of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or non-encapsulated perfumes.

The detergent composition according to the invention can be in bars or granular forms. The pH (measured in aqueous solution at use concentration) will usually be neutral or alkaline, e.g. in the range of 7–11.

An enzyme contained in the granule of the invention incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Surfactant System

The surfactant system may comprise nonionic, anionic, cationic, ampholytic, and/or zwitterionic surfactants. The surfactant system preferably consists of anionic surfactant or a combination of anionic and nonionic surfactant, e.g. 50–100% of anionic surfactant and 0–50% nonionic. The laundry detergent compositions may also contain cationic, ampholytic, zwitterionic, and semi-polar surfactants, as well as the nonionic and/or anionic surfactants other than those already described herein.

The surfactant is typically present at a level from 0.1% to 60% by weight. Some examples of surfactants are described below.

a) Nonionic Surfactant:

The surfactant may comprise polyalkylene oxide (e.g. polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensation products of primary and secondary aliphatic alcohols with from about 1 to about 25 moles of ethylene oxide, alkylpolysaccharides, and mixtures hereof. Most preferred are C8–C14 alkyl phenol ethoxylates having from 3 to 15 ethoxy groups and C8–C18 alcohol ethoxylates (preferably C10 avg.) having from 2 to 10 ethoxy groups, and mixtures thereof.

b) Anionic Surfactants:

Suitable anionic surfactants include the alkyl sulfate surfactants which are water soluble salts or acids of the formula ROSO3M wherein R preferably is a C10–C24 hydrocarbyl, preferably an alkyl or hydroxyalkyl having a C10–C20 alkyl component, more preferably a C12–C18 alkyl or hydroxyalkyl, and M is H or a cation, e.g., an alkali metal cation (e.g. sodium, potassium, lithium), or ammonium or substituted ammonium. Other anionic surfactants include salts (including, for example, sodium, potassium, ammonium, and substituted ammonium salts such as mono- di- and triethanolamine salts) of soap, C8–C22 primary or secondary alkanesulfonates, C8–C24 olefinsulfonates, sulfonated polycarboxylic acids prepared by sulfonation of the pyrolyzed product of alkaline earth metal citrates.

Alkylbenzene sulfonates are suitacble, especially linear (straight-chain) alkyl benzene sulfonates (LAS) wherein the alkyl group preferably contains from 10 to 18 carbon atoms. The laundry detergent compositions typically comprise from about 1% to about 40%, preferably from about 3% to about 20% by weight of such anionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate (EDTA), metal ion sequestrants such as aminopolyphosphonates. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP. Detergency builder salts are normally included in amounts of from 5% to 80% by weight of the composition. Preferred levels of builder for liquid detergents are from 5% to 30%.

Bleaching Agents

The detergent composition may also comprise a bleaching agents, e.g. an oxygen bleach or a halogen bleach. The oxygen bleach may be a hydrogen peroxide releasing agent such as a perborate (e.g. PB1 or PB4) or a percarbonate, or it may e.g. be a percarboxylic acid. The particle size of a bleaching agent may be 400–800 microns. When present, oxygen bleaching compounds will typically be present at levels of from about 1% to about 25%.

The hydrogen peroxide releasing agent can be used in combination with bleach activators such as tetra-acetylethylenediamine (TAED), nonanoyloxybenzene-sulfonate (NOBS), 3,5-trimethyl-hexsanoloxybenzene-sulfonate (ISONOBS) or pentaacetylglucose (PAG).

The halogen bleach may be, e.g. a hypohalite bleaching agent, for example, trichloro-isocyanuric acid and the sodium and potassium salt of dichloroisocyanurates and N-chloro and N-bromo alkane sulfonamides. Such materials are normally added at 0.5–10% by weight of the finished product, preferably 1–5% by weight.

Granular detergent compositions according to the present invention can also be in "compact form", i.e. they may have a relatively higher density than conventional granular detergents, i.e. form 550 to 950 g/l.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

More specifically, the enzyme containing granules of the invention may be incorporated in the detergent compositions described in WO 97/04079, WO 97/07202, WO 97/41212, and PCT/DK 97/00345.

MATERIALS AND METHODS

Preparation of Carrier Material

Portions of carrier material was prepared by spraying 3.0 kg of fibrous cellulose (Arbocel□ FTC200), 3.0 kg of kaolin (Speswhite□, English China Clay) and 20.5 kg of finely ground sodium sulfate with 9.5 kg of a 21% w/w aqueous solution of carbohydrate binder (Glucidex□ 21D, from Roquette Freres). This mixtures was granulated and dried as described in Example 1 in U.S. Pat. No. 4,106,991. The dry granulated carrier material was sieved, and the fraction between 0.3 and 1.0 mm was separated and used for further processing.

Absorbing Enzyme on the Carrier Material

The granulated and fractionated carrier material was transferred to a Lödiger mixer equipped with a multiple chopper head, and sprayed with a liquid Savinase™ enzyme concentrate solution approximately 33 KNPU/g containing 0.4% w/w g of a nonionic surfactant (Softanol 50). The enzyme containing solution was sprayet onto the carrier at dosage of 0.15 kg solution per kg carrier material. The nonionic surfactant was added to the enzyme concentrate to enhance the absorption of the enzyme onto the carrier. The Savinase□ concentrate was applied using a pressure nozzle submerged in the carrier and spraying directly into the chopper. The carrier and the Savinase™ concentrate was mixed by means of mixing blades and the mixing blades and the chopper were operated continuously during the spraying.

The resulting product was transferred to a Glatt WSG 15 fluid-bed apparatus (Glatt, Germany) with an air-inlet temperature of 62° C., and dried for 30 minutes, or until the product temperature exceeded 50° C., and then sieved on a 1.2 mm mesh screen, leaving only 0.8% w/w of residual, oversized particles on the sieve.

Measurement of Enzyme Stability

For each type of enzyme containing granule samples of the granules are mixed with a commercial detergent. One or of these samples are immediately sealed in glass jars and stored below −18° C. These samples are reference samples and the enzyme herein is by definition 100% stabile. Other samples are placed in climate controlled cupboards and stored for a preset period of time in open glass jars at different temperatures and humidities (% RH). When a preset storage period is finished samples are removed from the "climate static" conditions, and the glass jars immediately sealed and cooled to below −18° C. to stop any progressing inactivation of the enzyme. When all samples has been stored for the preset period of time, all samples including the reference samples are analyzed the day in an appropriate enzyme activity assay and the test results of the samples are calculated as percent of the reference sample test results.

Enzyme Assay

The enzyme assay used herein is a protease activity assay, and the unit for protease activity herein is Kilo Novo Protease Units per gram of sample (KNPU/g). The activity is determined relatively to an enzyme standard (Savinase™) of known activity. The enzyme standard is standardized by measuring for a given amount of enzyme the formation rate ($\mu$mol/minute) of free amino groups liberated from digestion of di-methyl-casein (DMC) in solution by the enzyme. The formation rate is monitored by recording the linear development of absorbance at 420 nm of the simultaneous reaction between the formed free amino groups and added 2,4,6-tri-nitro-benzene-sulfonic acid (TNBS). The digestion of DMC and the color reaction is carried out at 50° C. in a pH 8.3 boric acid buffer with a 9 min. reaction time followed by a 3 min. measuring time. A folder AF 220/1 is available upon request to Novo Nordisk A/S, Denmark, which folder is hereby included by reference.

For samples of the enzyme containing detergents and the standardized enzyme standard a modified assay was used, wherein the reaction was carried out at 40° C. in a pH 8.3 boric acid buffer containing 3.1 g/L boric acid (Merck), 11.18 g/L potassium chloride (Merck), 1.5 mL/L 15% BriJ 35 (Merck) and 20 g/L sodium sulfite bleach scavenger.

For measuring Endolase activity (a cellulase) any conventional endo cellulase viscosity reduction method may be used (such as the method described in B1087a-GB available upon request from Novo Nordisk A/S—Denmark). Endolase digests CMC (carboxy-methyl-cellulose) in solution thereby reducing the viscosity of the solution and the viscosity reduction is related to the activity of the endolase.

For measuring alfa-amylase activity (e.g. Natalase®) any conventional alfa-amylase assay may be used (such as the method described in AF318/1-GB available upon request from Novo Nordisk A/S—Denmark). Alfa-amylases cleaves 1–6 alfa bonds between adjacent glucose units. By using e.g. a 2-chlor-4-nitrophenyl-b-D-maltoheptaosid substrate and alfa- and beta-glucosidase enzymes the substrae may be completely digested into monosaccharides and 2-chlor-4-nitrophenol, which form a detectable colour. Kits for performing these assays are commercially available.

Measurement of Constant Humidity Values for Coating Compounds

The constant humidity of water soluble compound coating materials were measured by preparing a saturated aqueous solution with excess of solid phase of the compound in an open beaker. After equilibrium has been reached and no more of the compound dissolves in the liquid phase, and solid particles of the compound are still visible, the beaker is placed in a sealed thermostated humidity measuring device (e.g. a Novasina apparatus), which measures the % RH at the chosen temperature of the atmosphere over the saturated solution.

EXAMPLES

The invention disclosed herein is illustrated by the non-limiting examples given below

Example 1

A sample of the dry enzyme-loaded granular carrier was transferred to a Glatt WSG5 conventional fluid bed apparatus. Using a conventional top spray coating technique with an air inlet temperature of 70° C., air outlet temperature of 42° C. and with air volume of 600 m3/h the following steps were carried out in sequence:

a) an enzyme containing layer was applied onto the carrier by spraying an enzyme containing aqueous solution containing Savinase™, PVP/VA co-polymer (Luviscol VA64) and titaniumdioxide ($TiO_2$) onto the carrier at a spraying rate for the enzyme solution of 100 g/min. Approximately 210 g Savinase™ concentrate (30 KNPU/g), 2.34 g of PVP/VA co-polymer (Luviscol VA64) and 2.5 g of titaniumdioxide ($TiO_2$) were applied per kg carrier, b) a 80 g sodium citrate per kg carrier coating layer of was applied by spraying a 37% w/w aqueous solution of sodium citrate onto the product of a), at a spraying rate for the coating solution of 100 g/min, c) an additional coating layer of 50 g titaniumdioxide (Kronos 2044), 50 g kaolin (ECC Supreme), 55 g Glascol LS27 (46% suspension from Allied Colloids Ltd.—GB), 30 g PEG 4000 and 1.67 g Softanol 50 per kg carrier was applied by spraying an aqueous solution of these components onto the product of b), at a spraying rate for the coating solution of 100 g/min, and d) a final coating was applied by spraying a solution of 7.5 g PEG 4000 per kg carrier onto the product of c), at a spraying rate for the coating solution of 100 g/min.

The finished enzyme containing granule was dried for 5 minutes and then cooled to 30° C., where after it was removed from the fluid bed and sifted between 300 and 1200 µm As a reference two different types of granules were prepared. The first type of granule was prepared by repeating steps a)–d) with the exception that the coating described in b) was replaced by a 80 g ammonium sulfate per kg carrier coating layer by spraying a 37% w/w aqueous solution of ammonium sulfate onto the product of a), at a spraying rate for the coating solution of 100 g/min. The second type of granule was also prepared by repeating steps a)–d), but with the exception that the coating described in b) was replaced by a 80 g sodium formiate per kg carrier coating layer by spraying a 37% w/w aqueous solution of sodium formiate onto the product of a), at a spraying rate for the coating solution of 100 g/min.

Example 2

The storage stability of the enzyme containing granulates from Example 1 were tested in one powder detergent (A) containing perborate bleach and TAED and one powder detergent (B) containing percarbonate bleach. 100 mg samples of the enzyme containing granulates and 10.0 g samples of the detergents were mixed to constitute test samples. The samples were incubated in open jars at air conditions 35° C. and 55% RH in a thermostated and humidity controlled cupboard. Identical samples were taken out from the cupboard after 2 and 4 weeks and analyzed for enzyme (Savinase™) activity together with identical reference samples, which had been stored in sealed jars below −18° C. The results are given in Example 1, wherein the enzyme activities of the samples are given as a percentage of the corresponding reference samples.

TABLE 1

| | Coating compound | Residual activity in Detergent A | | Residual activity in Detergent B | |
|---|---|---|---|---|---|
| | | 2 weeks | 4 weeks | 2 weeks | 4 weeks |
| Invention granule | Sodium citrate | 76% | 51% | 82% | 69% |
| Reference granule | Ammonium sulfate | 56% | 39% | 70% | 59% |
| Reference granule | Sodium formiate | 35% | 21% | 32% | 21% |

Constant humidities at 25° C.: Ammonium sulfate=79; sodium formiate=56 and sodium citrate=86. The results show that the coating with highest constant humidity provides the best storage stability of the enzyme.

Example 3

The hygroscopicity.of the samples from Example 1 were tested including a reference sample which was identical to the granulates of Examples 1 to 3 except that it did not contain any salt coating of ammonium sulfate, sodium citrate or sodium formiate. All samples were incubated for 1 week in open jars at 3 different conditions: 55% RH and 35° C., 60% RH and 30° C. and 74% RH and 37° C. Subsequently the water absorption of the samples were determined by weighing the samples before and after the incubation. Further after the incubation the samples were examined under a microscope. The results are given in Table 2, which shows the water absorption of the samples at different humidities. These results clearly shows big difference in how much water is absorbed in identical granules with different coatings, indicating that sodium citrate has the lowest water absorbing properties (the highest constant humidity value). For comparison a sample of a granulate with a different core material and a coating of ammonium sulfate is included (Purafect G). This result shows that if the coating allows moisture to pass, the core may absorb huge amounts of water. Table 2 further lists the results of the microscope examination, which showed that the coating of some of the samples were damaged (cracks had developed) which was most clearly observed when the water absorption of the coating (absorption of the sample minus the absorption of the reference) had reached a level of approximately 50% of the salt layer weight (which constitutes 6% of total formula).

TABLE 2

| Sample | Coating (III) | % water absorption 55% RH | 60% RH | 70% RH | Coating damage observed at |
|---|---|---|---|---|---|
| Core material | no salt coating | 1.1 | 1.7 | 2.8 | No damage |
| reference granule | Ammonium sulfate | 1.4 | 2.2 | 6.1 | 70% RH |
| invention granule | Sodium citrate | 1.2 | 1.9 | 3.4 | No damage |
| Reference granule | Sodium formiate | 4.8 | 7.3 | 12.3 | 60% RH |
| Purafect G | Commercial product | 0.9 | 1.9 | 23.2 | Liquefies at 70% RH |

Constant humidities at 25° C.: Ammonium sulfate=79; sodium formiate=56 and sodium citrate=86.

Example 4

An enzyme containing granule coated with sodium citrate was produced as in Example 1 with the exception that the pH of the sodium citrate was adjusted to 7.5 by adding citric acid to the coating solution prior to the coating process.

Example 5

An enzyme containing granule was produced as in Example 4 with the exception that the coating of pure sodium citrate was replaced by a mixture of sodium citrate and sodium thiosulfate in the weight ratio 9:1. Thus a coating consisting of 72 g sodium citrate and 8 g thiosulfate per kg carrier was applied.

Example 6

An enzyme containing granule was produced as in Example 4 with the exception that the coating of pure sodium citrate was replaced by a mixture of sodium citrate and sodium thiosulfate in the weight ratio 4:1. Thus a coating consisting of 64 g sodium citrate and 16 g thiosulfate per kg carrier was applied.

Example 7

The storage stability of the enzyme containing granules from Examples 4–6 as well as the ammonium sulfate reference granule of Example 1 were tested in one powder detergent (A) containing perborate bleach and TAED and one powder detergent (B) containing percarbonate bleach. 100 mg samples of the enzyme containing granulates (Purafect 50 mg) and 10.0 g samples of the detergents were mixed to constitute test samples. The samples were incubated in open jars at air conditions 35° C. and 55% RH in a thermostated and humidity controlled cupboard. Identical samples were taken out from the cupboard after 2 and 4 weeks and analyzed for enzyme (Savinase™) activity together with identical reference samples, which had been stored in sealed jars below −18° C. The results are given in Example 3, wherein the enzyme activities of the samples are given as a percentage of the corresponding reference samples.

TABLE 3

| | Coating compound | Residual activity in Detergent A | | Residual activity in Detergent B | |
|---|---|---|---|---|---|
| | | 2 weeks | 4 weeks | 2 weeks | 4 weeks |
| Reference granule of (Ex. 1) | ammonium sulfate | 53% | 36% | 73% | 61% |
| Invention granule | Sodium citrate pH 7.5 | 80% | 51% | 74% | 68% |
| Invention granule | 90% Sodium citrate, 10% thiosulfate | 96% | 78% | 90% | 92% |
| Invention granule | 80% Sodium citrate, 20% thiosulfate | 103% | 89% | 95% | 92% |
| Purafect G | Commercial product | 89% | 79% | 90% | 81% |

Constant humidities at 25° C.: Ammonium sulfate=79 and sodium citrate=86.

Example 8

An enzyme containing granule was produced as in Example 1 with the exception that i) the enzyme solution used for both absorption of enzyme onto the carrier and for applying the enzyme layer contained sodium thiosulfate in an amount corresponding to 0.33% w/w of the final coated granulate and ii) the sodium citrate coating was replaced by a 80 g per kg carrier sodium sulfate coating by applying a 45° C., 28.6% w/w aqueous sodium sulfate solution.

Further a reference granule was prepared identical to the first granule in this example with the exception that the sodium sulfate coating was replaced with a 80 g per kg carrier coating of ammonium sulfate.

Example 9

The storage stability of the enzyme containing granules from Example 8 were tested along with a commercial product in one powder detergent (A) containing sodium perborate bleach and TAED, one powder detergent (B) containing sodium percarbonate bleach and one powder detergent (C) without bleach. 100 mg samples (50 mg Purafect G) of the enzyme containing granulates and 10.0 g samples of the detergents were mixed to constitute test samples. The bleach containing samples were incubated in open jars at air conditions 35° C. and 55% RH, while the samples without bleach were incubated in open jars at air conditions 37° C. and 70% RH. All samples were incubated in thermostated and humidity controlled cupboards. Identical samples were taken out from the cupboard after 2 and 4 weeks and analyzed for enzyme (Savinase™) activity together with identical reference samples, which had been stored in sealed jars below −18° C. The results are given in Table 4, wherein the enzyme activities of the samples are given as a percentage of the corresponding reference samples.

TABLE 4

| | Coating compound | Residual activity in Detergent A | | Residual activity in Detergent B | |
|---|---|---|---|---|---|
| | | 2 weeks | 4 weeks | 2 weeks | 4 weeks |
| Reference granule | ammonium sulfate | 68% | 49% | 87% | 78% |
| Invention granule | Sodium sulfate | 90% | 72% | 98% | 100% |
| Purafect G | commercial product | | | 92% | 83% |

| | Coating compound | Residual activity in Detergent C | |
|---|---|---|---|
| | | 2 weeks | 4 weeks |
| Reference granule | ammonium sulfate | 74% | 53% |
| Invention granule | Sodium sulfate | 93% | 92% |
| Purafect G | Commercial product | 83% | 47% |

Constant humidities at 25° C.: Ammonium sulfate=79; sodium sulfate=93.

The results show that coating materials with higher constant humidity results in improved stability.

Example 10

An enzyme containing granule coated with sodium sulfate was produced as in Example 8 with the exception that a different ultra filtrated Savinase™ concentrate solution (app 41 KNPU/g) was used throughout the process.

Example 11

A sample of dry enzyme-loaded granular carrier was produced as described vide supra with the exception that the enzyme solution used for absorbing enzyme onto the carrier was added 5.33 g of sodium thiosulfate per kg finished dry carrier. The enzyme and thiosulfate loaded carrier was transferred to a Glatt WSG5 conventional fluid bed apparatus. Using a conventional top spray coating technique with an air inlet temperature of 70° C., air outlet temperature of 42° C. and with air volume of 600 m3/h the following steps were carried out in sequence:

a) an enzyme containing layer was applied onto the carrier by spraying an enzyme containing aqueous solution containing Savinase™, PVP/VA co-polymer (Luviscol VA64), titaniumdioxide ($TiO_2$) and sodium thiosulfate onto the carrier at a spraying rate of 100 g/min. Approximately 87 g Savinase™ concentrate (41 KNPU/g), 2.67 g of PVP/VA co-polymer (Luviscol VA64), 1.67 g of titaniumdioxide ($TiO_2$) and 1.67 g sodium thiosulfate were applied per kg carrier, b) a 267 g sodium sulfate per kg carrier coating layer of sodium sulfate was applied by spraying a 28.5% w/w aqueous solution of sodium sulfate at approximately 45° C. onto the product of a), at a spraying rate for the coating solution of 100 g/min, c) a final lubricant coating was applied by spraying a solution of 7.33 g PEG 4000 per kg carrier onto the product of c), at a spraying rate of 100 g/min.

The finished enzyme containing granulate was dried for 5 minutes and then cooled to 30° C., where after it was removed from the fluid bed and sifted between 300 and 1200 μm

Example 12

The storage stability of the enzyme containing granulates from Examples 13 and 14 were tested along with two commercial products in one powder detergent (A) containing perborate bleach and TAED, one powder detergent (B) containing percarbonate bleach and one powder detergent (C) without bleach. 150 mg samples of the enzyme containing granulates (75 mg Purafect E and G) and 10.0 g samples of the detergents were mixed to constitute test samples. The bleach containing samples were incubated in open jars at air conditions 35° C. and 55% RH, while the samples without bleach were incubated in open jars at air conditions 37° C. and 70% RH. All samples were incubated in thermostated and humidity controlled cupboards. Identical samples were taken out from the cupboard after 2 and 4 weeks and analyzed for enzyme (Savinase™) activity together with identical reference samples, which had been stored in sealed jars below −18° C. The results are given in Table 5, wherein the enzyme activities of the samples are given as a percentage of the corresponding reference samples.

TABLE 5

| | Coating compound | Residual activity in Detergent A | | Residual activity in Detergent B | |
|---|---|---|---|---|---|
| | | 2 weeks | 4 weeks | 2 weeks | 4 weeks |
| Invention granule (Ex. 10) | Sodium sulfate | 82% | 55% | 85% | 77% |
| Invention granule (Ex. 11) | Sodium sulfate | 98% | 98% | 96% | 96% |
| Purafect E | commercial product | 88% | 65% | 51% | 41% |
| Purafect G | commercial product | 95% | 75% | 73% | 62% |
| Purafect G | Commercial product | — | — | | |

| | Coating compound | Residual activity in Detergent C | |
|---|---|---|---|
| | | 2 weeks | 4 weeks |
| Invention granule (Ex. 10) | sodium sulfate | 94% | 80% |
| Invention granule (ex. 11) | sodium sulfate | 99% | 95% |
| Purafect E | commercial product | 65% | 17% |

The results given in Table 5 shows that application of a thick coating of with a high constant humidity leads to superior stability even if only a lubricant is applied as an additional coating.

Example 13

20 kg of uncoated Savinase® (protease enzyme) containing granulate (type TX) was produced as described in U.S. Pat. No. 4,106,991 Example 1 with the following exceptions:

1) sodium sulfate was used in stead of sodium chloride as filler material 2) the enzyme concentrate was an aqueous suspension of crystalline enzyme containing also a binder (Glucidex) and 0.4% w/w methionine as an antioxidant The uncoated enzyme granule was transferred to a 50 litre Lödige mixer and sprayed with 2.0 kg of a solution/suspension consisting of 25% sodium sulfate, 12% dextrine, 7% TiO2 and 56% of water. The granular mass was during the spraying treated with the chopper as described in U.S. Pat. No. 4,106,991.

The mixer treated granulate was subsequently transferred to a Glatt WSG5 fluid bed and dried. 15 kg of the dried granulate was thereafter successively coated in three steps with parameters as described in Example 1.

a) the enzyme containing granulate was in a first step coated with 11.0 kg of a solution/suspension consisting of 27.1% sodium sulfate 3.9% TiO2, 1.0% dextrin and water ad 100%. The salt solution was during the spraying kept at 45–50° C. to avoid crystallisation of the sodium sulfate. The coated the enzyme containing granule with a coating containing 85% w/w sodium sulfate.

b) an additional coating was applied as a dust suppressing film by spraying with 3.5 kg of a solution consisting of 6.3% methylhydroxypropyl cellulose (Aqualon 8MP5C) 6.3% PEG 4000 and water ad 100% c) the granulate was in a final step sprayed with 0.46 kg of a 24% PEG 4000/water solution.

Example 14

A comparative base granulate was prepared as described in Example 13 without the mixer treatment and without fluid bed coatings and was conventionally coated as described in U.S. Pat. No. 106,991 Example 22 by applying a solution of 7% PEG 4000 and 12.5% of a 1:1 TiO2/Kaolin mixture.

Example 15

The storage stability of granulates of Examples 13 and 14 was tested in a perborate containing (A) and a percarbonate containing (B) detergent as described in Example 4.

TABLE 6

|  | Coating compound | Residual activity in detergent A | | Residual activity in detergent B | |
| --- | --- | --- | --- | --- | --- |
|  |  | 2 weeks | 4 week | 2 weeks | 4 weeks |
| Example 13 granulate | Sodium sulfate | 98 | 92 | 103 | 99 |
| Example 14 granulate | comparative granule | 69 | 43 | 63 | 48 |
| Purafect G | Commercial product | 90 | 73 | 97 | 83 |

Example 16

15 kg of dry Savinase enzyme absorbed on a granular carrier was transferred to a Glatt WSG conventional fluid bed apparatus. Using a conventional top spray coating technique with an air inlet temperature of 70° C. and an air outlet of 42° C. and with an air volume air volume of 600 m³/h were the following steps carried out in sequence:

a) an enzyme containing layer was applied onto the carrier by spraying granular carrier with an enzyme containing solution consisting of 2.07 kg of a liquid Savinase concentrate (82% dry matter, 24 KNPU/g), 50 g Glucidex 21D and 54 g TiO2 and with a spraying rate of 100 g/min.

b) The salt layer was applied in a second step by spraying with 14.7 kg of a solution consisting of 27% sodium sulfate, 3.9% TiO2, 1,0% Glucidex 21D and water ad 100%. The temperature of the solution was kept at 45–50° C. to avoid crystallisation of the salt.

c) The salt coated granulate was in a next step coated with a dust suppressing film by spraying with 3.4 kg of a solution consisting of 6.3% methylhydroxypropyl cellulose, 6.3% PEG 4000 and water ad 100%.

d) the granulate was in a final step sprayed with 0.46 kg of a 24% PEG 4000/water solution.

All enzyme concentrate used for this preparation had an addition of sodium thiosulfate to the concentrate corresponding to 0.3% w/w of the final granulate.

Example 17

This example was prepared as Example 16 with the exception that the solution for the coating (b) was reduced to 11,0 kg.

Example 18

This example was prepared as Example 16 with the exception that the solution for the coating (b) was reduced to 7.35 kg.

Example 19

This example was produced according to Example 16 step (a), i.e. without the salt coating and the dust suppressing film.

Example 20

The storage stability of granulates of Examples 16–19 was tested and compared to references in three detergents as described in Example 9.

TABLE 7

|  |  | Residual activity (%) in detergent A | | Residual activity (%) in detergent B | |
| --- | --- | --- | --- | --- | --- |
|  | Coating compound | 2 weeks | 4 week | 2 weeks | 4 weeks |
| Example 16 | Sodium sulfate | 99 | 99 | 98 | 98 |
| Example 17 | Sodium sulfate (75% relative to Example 16) | 100 | 96 | 94 | 97 |
| Example 18 | Sodium sulfate 50% relative to Example 16) | 97 | 94 | 96 | 97 |
| Example 19 | Comparative granule without sodium sulfate | 60 | 44 | 55 | 43 |
| Example 14 | Comparative granule | 69 | 43 | 63 | 48 |
| Purafect G | Commercial product | 90 | 73 | 97 | 83 |

|  | Coating compound | Residual activity (%) in detergent C | |
| --- | --- | --- | --- |
|  |  | 2 weeks | 4 week |
| Example 16 | Sodium sulfate | 94 | 82 |
| Example 17 | Sodium sulfate (75% relative to Example 16) | 92 | 71 |
| Example 18 | Sodium sulfate (50% relative to Example 16) | 93 | 76 |
| Example 19 | Comparative granule without sodium sulfate | 79 | 49 |
| Example 14 | Comparative granule | 88 | 62 |
| Purafect G | Commercial product | 89 | 47 |

Example 21

An Endolase (cellulase enzyme) containing granulate was produced as described in U.S. Pat. No. 4,106,991 Example 1 with the following exceptions:

a) The filler was sodium sulfate
b) The liquid enzyme concentrate was used as the granulating liquid.
c) The granulate had furthermore an addition of 10% w/w of a carbohydrate binder and 0.5% w/w of sodium thiosulfate.

The granulate was conventionally coated as described in U.S. Pat. No. 106,991 Example 22 by applying a solution of 7.2% w/w PEG 4000 and 13,0% w/w of a 1:1 mixture of TiO2 and kaolin.

Example 22

An Endolase (cellulase enzyme) containing granulate was produced as described in Example 21. This base granulate was coated according to the steps (b)–(d) in Example 16 with the exception that 10.6 kg of the salt solution was applied in step (b).

Example 23

The storage stability of granulates of Examples 21 and 22 was tested in a sodium perborate containing detergent (A) with conditions as described in Example 9.

Table 8

|  | Coating compound | Residual activity (%) in detergent A | | |
|---|---|---|---|---|
|  |  | 1 week | 3 weeks | 5 weeks |
| Example 21 | Comparative granule | 97 | 28 | 23 |
| Example 22 | Sodium sulfate |  | 100 | 70 |

Example 24

A Natalase® (an amylase enzyme) containing granulate was produced as described in U.S. Pat. No. 4,106,991 Example 1 with the following exceptions:
1) sodium sulfate was used in stead of sodium chloride as filler material
2) the enzyme concentrate was an aqueous suspension of crystalline enzyme which was also used as the granulating liquid containing also a binder (Glucidex).
3) The granulate had furthermore an addition of 0.4% w/w sodium thiosulfate (calculated as % of the uncoated granulate).

The granulate was conventionally coated as described in U.S. Pat. No. 106,991 Example 22 by applying a solution of 7% of PEG 4000 and 12.5% of a 1:1 mixture of TiO2 and kaolin.

Example 25

A Natalase® containing granulate was produced as described in Example 24. 1300 g of the Natalase containing base granulate was transferred to a UniGlatt fluid bed where coated with a salt coating by spraying it with a 50° C. salt solution at consisting of:
234 g of sodium sulfate
9 g of Glucidex 21D
25 g of TiO2
585 g of water The spraying conditions were air inlet temperature 70° C. and air outlet temperature 42° C. The granulate was after finishing the spraying further dried in the fluid bed for 5 minutes

Example 26

The storage stability of granulates of Examples 24 and 25 was tested in the percarbonate containing detergent (B) with conditions as described in Example 9.

TABLE 9

|  | Coating compound | Residual activity in detergent B | | |
|---|---|---|---|---|
|  |  | 1 week | 2 weeks | 4 weeks |
| Example 24 | Comparative granule | 82 | 79 | 69 |
| Example 25 | Sodium sulfate | 98 | 97 | 94 |

Example 27

A non-coated Savinase® containing granulate (granulate A) was produced as described in U.S. Pat. No. 4,106,991 Example 1 wit the following exceptions:
1) sodium sulfate was used in stead of sodium chloride as filler material
2) the enzyme concentrate was an aqueous suspension of crystalline enzyme containing also a carbohydrate binder (Glucidex) and methionine as an antioxidant The non-coated granules was coated with a salt layer using a fluid bed according to the following procedure:
a) 15 kg of the uncoated granules were fluidized in a Glatt WSG-5 fluid bed using 550 m³ air per hour. The air inlet temperature was 70° C.
b) A salt solution of 2.0 kg $Na_2SO_4$ dissolved in 5.0 kg water at 50° C. was prepared. 2.1 kg of this solution was sprayed onto the fluidized granules at a rate of 100 grams solution per minute. During spraying of the liquid the product temperature was approximately 42° C. After adding the solution the water was allowed to evaporate from the coated granules (until the product temperature raised quickly in the fluid bed). A sample of 2.0 kg (granulate A1) of the coated granules was taken out and the coating process was repeated to add further coating to the granules remaining in the fluid bed by spraying the remaining granules with an additional 1.75 kg of the salt solution. A sample of 2.0 kg of the additionally coated granules (granulate A2) was taken out and the coating process was repeated once more to add even further coating to the granules remaining in the fluid bed by spraying the remaining granules with the remaining 3.15 kg of the salt solution (granulate A3).

Example 28

The enzyme stability in the granules were tested in a model powder detergent containing Sodium Perborate at 35° C. and 55% relative humidity in open boxes according to Example 9.

TABLE 10

| Granulate | Residual Savinase activity in % | |
| --- | --- | --- |
| | 2 weeks | 4 weeks |
| Uncoated Savinase ® granules | 47 | 36 |
| A1 (4.0% Na$_2$SO$_4$) | 68 | 42 |
| A2 (7.8% Na$_2$SO$_4$) | 77 | 55 |
| A3 (15.8% Na$_2$SO$_4$) | 92 | 75 |

The % salt was calculated as % w/w salt of the uncoated granules under the condition that all water was evaporated. From Example 10 it was concluded that the enzyme stability in the Savinase® granules were significantly improved by the salt coating and that increasing the amount of salt improves the stability.

What is claimed is:

1. An enzyme containing granule comprising:
    a) an enzyme containing core; and
    b) a protective substantially continuous layer or coating encapsulating the core comprising at least 65% of a water soluble compound selected from the group consisting of alkali or earth alkali metal ion salt of phosphate, having a molecular weight below 500 grams per mole, a pH below 11 and a constant humidity at 20° C. of more than 81%.

2. The granule according to claim 1, wherein said water soluble compound has a molecular weight between 30–500 g/mole.

3. The granule according to claim 1, wherein said water soluble compound has a molecular weight between 75–400 g/mole.

4. The granule according to claim 1, wherein said water soluble compound has a solubility of at least 0.1 gram per 100 gram water.

5. The granule according to claim 1, wherein said water soluble compound has a solubility of at least 10 gram per 100 gram water.

6. The granule according to claim 1, wherein said water soluble compound has constant humidity at 20° C. of more than 90%.

7. The granule according to claim 1, wherein said core is a non absorbing core.

8. The granule according to claim 1, wherein said coating further comprises one or more protective agents capable of inactivating components hostile to the enzyme entering the granule from a surrounding matrix.

9. The granule according to claim 8, wherein said hostile component is a detergent bleach component.

10. The granule according to claim 8, wherein said protective agent is selected from the group consisting of reducing agents, antioxidants and salts of transition metals.

11. The granule according to claim 10, herein said reducing agent is a salt of thiosulfate.

12. The granule according to claim 1, wherein said coating constitutes 1–75% w/w of the coated granule.

13. The granule according to claim 1, wherein said enzyme containing core comprises a particulate carrier and an enzyme containing layer.

14. The granule according to claim 13, wherein additional enzyme is adsorbed into the carrier.

15. The granule according to claim 14, wherein said absorbed enzyme and/or enzyme containing layer comprises a protective reducing agent.

16. The granule according to claim 1, wherein said enzyme is selected from the group consisting of oxidoreductases, transferases, hydrolases, lyases, isomerases and ligases.

17. The granule according to claim 1, further comprising an additional coating.

18. The granule according to claim 17, wherein said additional coating is a lubricant.

19. A method for producing the granule of claim 1, comprising:
    a) mixing an enzyme containing core material with a liquid medium comprising said water soluble compound; and
    b) removing volatile components of the liquid medium from the mixture, so as to deposit the nonvolatile components of the liquid medium as solid coating layer on the core material.

20. The method according to claim 19, wherein the granule is obtained by a fluid bed process comprising:
    a) fluidising an enzyme containing core material in a fluid bed apparatus,
    b) introducing a liquid medium comprising the water soluble compound of the invention by atomization into the fluid bed, so as to deposit the nonvolatile components of the liquid medium as solid coating layer on the core material and,
    c) removing volatile components of the liquid medium from the coated core material.

21. A detergent composition comprising the enzyme containing granular composition of claim 1.

22. A cleaning method comprising contacting an object with an aqueous solution comprising the particulate composition of claim 1.

* * * * *